United States Patent [19]

Thornfeldt

[11] Patent Number: 4,885,282

[45] Date of Patent: Dec. 5, 1989

[54] TREATMENT OF HYPERHIDROSIS, ICHTHYOSIS AND WRINKLING

[76] Inventor: Carl R. Thornfeldt, 1054 NW. 2nd Ave., Ontario, Oreg. 97914

[21] Appl. No.: 160,042

[22] Filed: Mar. 8, 1988

Related U.S. Application Data

[63] Continuation-in-part of Ser. No. 69,071, Jul. 2, 1987, abandoned.

[51] Int. Cl.$^4$ .................... H61K 31/19; H61K 31/715
[52] U.S. Cl. ..................................... 514/53; 514/547; 514/552; 514/574; 514/558
[58] Field of Search ................... 514/574, 53, 547, 552

[56] References Cited

U.S. PATENT DOCUMENTS

| | | | |
|---|---|---|---|
| 4,292,326 | 9/1981 | Nazzaro-Porro | 424/317 |
| 4,386,104 | 5/1983 | Nazzaro-Porro | 424/317 |
| 4,713,394 | 12/1987 | Thornfeldt | 514/574 |

OTHER PUBLICATIONS

J. S. Weiss et al., "Topical Tretinoin Improves Photoaged Skin," *JAMA*, vol. 259, No. 4, pp. 527–532, (1988).

J. F. Morgan et al., "Studies on the In Vitro Antitumor Activity of Fatty Acids," *Can. J. Biochem. Physiol.*, vol. 38, pp. 597–603, (1960).

A. Kato et al., "Antitumor Activity of Monoglycerides and Other Esters of Fatty Acids," *J. Antibiotics*, vol. XXII, No. 2, pp. 83–84, Feb. 1969.

G. Medes et al., "Metabolism of Neoplastic Tissue.," *J. Nntl. Cancer Inst.*, vol. 24, No. 1, pp. 1–12, Jan. 1960.

*Primary Examiner*—Leonard Schenkman
*Attorney, Agent, or Firm*—Townsend and Townsend

[57] ABSTRACT

Skin suffering from emotional hyperhidrosis, ichthyosis with or without keratosis, and intrinsic or photoaging wrinkling is treated with mono- or discarboxylic acids containing 4 to 18 carbon atoms, or certain mercapto derivatives, salts or esters thereof.

27 Claims, No Drawings

TREATMENT OF HYPERHIDROSIS, ICHTHYOSIS AND WRINKLING

CROSS-REFERENCE TO RELATED APPLICATION

This application is a continuation-in-part of co-pending application Ser. No. 69,071, filed July 2, 1987 now abandoned.

BACKGROUND AND SUMMARY OF THE INVENTION

This invention relates to the treatment of hyperhidrosis, ichthyosis, and wrinkling of the skin. In particular, this invention is directed toward conditions involving hyperactivity of the adnexa and the epidermis, excessive cellular aggregation within the epidermis and stratum corneum, and photoaging or dermatoheliosis.

The present invention resides in the discovery that certain mono- and dicarboxylic acids and their esters are effective in the treatment of these conditions, and represents a departure from the types of skin conditions on which such acids have previously been effective.

U.S. Pat. Nos. 4,292,326 (Nazarro-Porro, Sept. 29, 1981) and 4,386,104 (Nazarro-Porro, May 31, 1983) disclose the use of dicarboxylic acids in the treatment of acne and melanocytic hyperpigmentary dermatoses.

Emotional hyperhidrosis, which is the most common form of hyperhidrosis, is a noninflammatory exaggerated sweating response that comprises one socially or at work. The eccrine sweat glands of the axilla and volar aspects, palms and soles, are most often affected. Occasionally, the response is seen on the upper lip or forehead. Localized areas of involvement outside of the axillae and volar aspects are often referred to as an eccrine nevus. Axillary and volar hyperhidrosis may coexist in a given patient, but usually one site predominates and requires therapy.

Axillary hyperhidrosis may be quite mild and controlled by frequent use of antiperspirants. Volar hyperhidrosis often begins in infancy or childhood while the axillary type begins between 15 and 18 years of age. Current therapies are usually discouraging due to poor results and/or significant side effects.

Volar hyperhidrosis therapy includes two topical agents and systemic anticholinergics that have no effect on the axillary type. Topical formaldehyde is limited by being a common allergic sensitizer while topical glutaraldehyde produces a brownish stain. Systemic cholinergic agents like Robinul (a trade name for glycopyrrolate, a known anticholinergic available from A.H. Robins Company, Pharmaceutical Division, Richmond, Va.) are occasionally helpful but usually produce unpleasant side effects at therapeutic doses.

Two topical products are generally effective in both types of hyperhidrosis. Topical aluminum chloride hexahydrate has been linked to Parkinson's and Alzheimer's diseases. Ionopharesis is reasonably effective but requires cumbersome electrical ion exchange machines. Sympathectomy is a very aggressive surgical procedure effective to some degree in both types but presenting a very high risk. Selective surgical excision of overactive axillary sweat glands is often successful but most patients are reluctant to have such a procedure performed.

Ichthyosis vulgaris, the most common of the ichthyoses, is the most common disorder of keratinization. It usually starts in childhood and is characterized by "fish scales" and keratosis pilaris most prominent on the extremities. Other common findings include scaling of the lower back and abdomen with hyperkeratosis of the feet. This disorder results from excessive aggregation of keratinocytes. Current lifelong therapy consists of emollients, including most standard ones which are poorly effective, and alpha hydroxy acids which may produce burning sensations, especially in children. Propylene glycol, a common allergic sensitizer and irritant, is also reported to be effective, but has obvious disadvantages. Alpha hydroxy acids are distinct chemically from dicarboxylic acids in that they are short chain (3 to 5 carbon) compounds without an associated mono-, di-, or tricarboxylic moiety at either end.

Keratosis pilaris, generally considered to be a local follicular subset of ichthyosis vulgaris, consists of a horny plug containing inspissated sebrum and epithelial cells with a coiled hair filling the follicular infundibulum usually on the proximal extremities. The majority of atopic individuals and those afflicted with ichthyosis vulgaris display keratosis pilaris. The current treatment regimens utilizing emollients, keratolytics, and tretinoin are often disappointing despite prolonged treatment.

Wrinkling of the skin results from a combination of intrinsic thinning and photoaging (dermatoheliosis), with the latter being the primary cause. One compound, transretinoic acid, has been proven to reverse such structural damage with topical application.

These are examples of conditions for which it has been discovered that dicarboxylic acids within the scope of the present invention are an effective treatment when applied topically. In general, the invention applies to adnexal and epidermal hyperactive production and excessive epidermal aggregation disease states such as hyperhidrosis and the ichthyoses.

DETAILED DESCRIPTION OF THE INVENTION

The mono- and dicarboxylic acids of the present invention are those having 4 to 18 carbon atoms, inclusive. Preferred such acids are noncyclic acids and saturated aliphatic acids, particularly straight-chain species. Those having 7–13 carbon atoms are the most preferred. Examples include azelaic (1,9-nonanedioic) acid, suberic (1,8-octanedioic) acid, sebacic (1,10-decanedioic) acid, and pimelic (1,7-heptanedioic) acid. The invention also extends to mercapto derivatives of such acids, including mono- and dimercapto derivatives, as well as salts such as, for example, sodium, and esters. Included among the esters are alkyl esters and esters prepared from polyols and oligo- and polysaccharides. Examples of such polyols are glycerol, polyethylene glycol and polypropylene glycol, and examples of oligo- and polysaccharides are sucrose, lactose and starch. Esters of the dicarboxylic acids include both monoesters and diesters. Preferred esters, particularly for the dicarboxylic acids, are monoglycerides and sucrose monoesters.

The compounds are generally applied in dermatological formulations. These include any of the various known mixtures and combinations which may be applied topically and which will permit even spreading of the active ingredient over the affected area. Examples include creams, lotions, solutions, ointments and unguents.

The concentration of the mono- or dicarboxylic acid in the formulation is not critical and may vary over a wide range. The acid concentration may indeed range as high as the upper limit of dissolvability in any given formulation. In most cases, however, best results are achieved within a range of about 0.1% to about 40% be weight, preferably from about 3% to about 20% by weight.

The formulation may contain additional ingredients on an optional basis, including both those which are biologically active and those which are biologically inactive. Examples of inactive ingredients are wetting agents, surfactants, emollients, solvents, keratolytics, and percutaneous absorption enhancers.

The term "therapeutically effective amount" is used herein to denote any amount which will cause a substantial improvement or change in the condition for which it is applied when applied to the affected area repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The compositions are generally applied in topical manner to the affected area, i.e., localized application to the skin region where the clinical abnormality is manifest.

The following examples are offered for illustrative purposes, and are intended neither to limit nor define the invention in any manner.

EXAMPLE 1 - FORMULATIONS

Formulation A: A vessel was charged with 10 grams of azelaic acid and 10 milliliters of absolute ethyl alcohol, and heated slowly until warm. To the resulting solution was added 50 milliliters of Vehicle/N or Solvent G. These are identical nonprescription solvent mixtures consisting of 47.5% ethyl alcohol, 4% isopropyl alcohol and purified water, laureth-4, and propylene glycol. Vehicle/N is obtained from Neutrogena Dermatologicals of Los Angeles, Calif. Solvent G is obtained from Syosset Laboratories, Inc. of Syosset, N.Y.

Formulation B: One pound of Cetaphil cream and 90 grams of azelaic acid were heated separately until each was liquified (approximately two hours). Cetaphil cream is a commercially available nonprescription mixture of water, ethyl alcohol, propylene alcohol, sodium lauryl sulfate, stearyl alcohol, methylparaben, propylparaben and butylparaben obtainable from Owen Laboratories, San Antonio, Tex. Once the cream and acid were liquified, the acid was slowly beat into the cream to form a smooth homogeneous cream.

EXAMPLE 2 - APPLICATION

Three patients with emotional hyperhidrosis of the palms (two patients) and axilla (one patient) were treated in accordance with the present invention. These patients had failed to respond to systemic anticholinergics and topical Drysol (a 20% w/v solution of $AlCl_3.6H_2O$ in anhydrous ethyl alcohol, a known drug for use as an aid in the management of hyperhidrosis, available from Person & Covey, Inc., Glendale, Calif.). The treatment consisted of twice daily application of Formulation A occluded with plastic at night. In the cases of two of the patients, the conditions were completely resolved within six to eight weeks. The other patient improved over 75% within nine weeks. All three continue to apply the formulation once or twice weekly to keep the condition in remission.

EXAMPLE 3 - APPLICATION

Two patients with ichthyosis vulgaris that did not respond to standard emollients were treated with Formulation B two to three times daily. One patient had not responded to alpha hydroxy acid preparations and the other, a child, had experienced burning discomfort when these agents were applied. The child's skin returned to normal texture in five weeks, and the skin of the other patient returned to normal in seven weeks. After the skin cleared, both patients continued to use the preparation every other day to prevent recurrence, with successful results.

EXAMPLE 4 - APPLICATION

Three patients, one male physician age 72 and two women ages 66 and 67 each applied Formulation B once daily for between nine and eleven and one-half months to treat and prevent sun-induced facial precancers and sebhorreic dermatitis. All three remarked that in addition to the correction of these conditions, the formulation improved the skin texture and the suppleness of their face skin. Examination confirmed these observations; two were further supported by photographic evidence.

The foregoing description is offered primarily for purposes of illustration. It will be readily apparent to those skilled in the art that numerous variations in both the formulations and their method of use, not mentioned above, may be made without departing from the spirit and scope of the invention.

What is claimed is:

1. A method for the treatment of skin suffering from hyperhidrosis, ichthyosis or wrinkling, said method comprising applying to the affected area a therapeutically effective amount of a compound selected from the group consisting of mono- and dicarboxylic acids having 4 to 18 carbon atoms, mercapto derivatives thereof, salts thereof, and esters thereof.

2. A method in accordance with claim 1 in which said mono- and dicarboxylic acids are straight-chain.

3. A method in accordance with claim 1 in which said mono- and dicarboxylic acids are straight-chain and contain 7 to 13 carbon atoms.

4. A method in accordance with claim 1 in which said compound is a straight-chain dicarboxylic acid having 7 to 13 carbon atoms.

5. A method in accordance with claim 1 in which said compound is selected from the group consisting of azelaic acid, mercapto derivatives thereof, salts thereof, and esters thereof.

6. A method in accordance with claim 1 in which said esters are selected from the group consisting of alkyl esters and esters prepared from polyols, oligosaccharides and polysaccharides.

7. A method in accordance with claim 1 in which said esters are selected from the group consisting of polyols and oligosaccharides.

8. A method in accordance with claim 1 in which said esters are selected from the group consisting of glycerol, polyethylene glycol, polypropylene glycol and sucrose.

9. A method in accordance with claim 1 in which said compound is a member selected from the group consisting of monoglyceride and monosucrose esters of dicarboxylic acids having 4 to 18 carbon atoms.

10. A method in accordance with claim 1 in which said compound is azelaic acid.

11. A method in accordance with claim 1 in which said compound is a member selected from the group consisting of monoglyceride and monosucrose esters of azelaic acid.

12. A method in accordance with claim 1 in which said compound is in the form of a dermatological formulation of which said compound comprises from about 0.1% to about 40% by weight.

13. A method in accordance with claim 1 in which said compound is in the form of a dermatological formulation of which said compound comprises from about 3% to about 20% by weight.

14. A method in accordance with claim 1 in which said compound is applied topically in a form selected from the group consisting of a lotion, a cream, an unguent, an ointment and a solution.

15. A method for the treatment of skin suffering from hyperhidrosis, said method comprising applying to the affected area a therapeutically effective amount of a dermatological formulation containing from about 0.1% to about 40% by weight of a compound selected from the group consisting of mono- and dicarboxylic acids having 4 to 18 carbon atoms, mercapto derivatives thereof, salts thereof, and polyol and oligosaccharide esters thereof.

16. A method in accordance with claim 15 in which said compound is a member selected from the group consisting of dicarboxylic acids having 7 to 13 carbon atoms, mercapto derivatives thereof, salts thereof, and polyol and oligosaccharide esters thereof.

17. A method in accordance with claim 15 in which said compound is a member selected from the group consisting of azelaic acid, the monoglyceride ester and the monosucrose ester thereof.

18. A method for the treatment of skin suffering from ichthyosis, said method comprising applying to the affected area a therapeutically effective amount of a dermatological formulation containing from about 0.1% to about 40% by weight of a compound selected from the group consisting of mono- and dicarboxylic acids having 4 to 18 carbon atoms, mercapto derivatives thereof, salts thereof, and polyol and oligosaccharide esters thereof.

19. A method in accordance with claim 18 in which said compound is a member selected from the group consisting of dicarboxylic acids having 7 to 13 carbon atoms, mercapto derivatives thereof, salts thereof, and polyol and oligosaccharide esters thereof.

20. A method in accordance with claim 18 in which said compound is a member selected from the group consisting of azelaic acid, the monoglyceride ester and the monosucrose ester thereof.

21. A method for the treatment of skin suffering from keratosis pilaris, said method comprising applying to the affected area a therapeutically effective amount of a dermatological formulation containing from 0.1% to about 40% by weight of a compound selected from the group consisting of mono- and dicarboxylic acids having 7 to 13 carbon atoms, mercapto derivatives thereof, salts thereof, and polyol and oligosaccharide esters thereof.

22. A method in accordance with claim 21 in which said compound is a member selected from the group consisting of dicarboxylic acids having 7 to 13 carbon atoms, mercapto derivatives thereof, salts thereof, and polyol and oligosaccharide esters thereof.

23. A method in accordance with claim 21 in which said compound is a member selected from the group consisting of azelaic acid, the monoglyceride ester and the monosucrose ester thereof.

24. A method for the treatment of skin suffering from wrinkling due to intrinsic aging or photoaging, said method comprising applying to the affected area a therapeutically effective amount of a dermatological formulation containing from 0.1% to about 40% by weight of a compound selected from the group consisting of mono- and dicarboxylic acids having 7 to 13 carbon atoms, mercapto derivatives thereof, salts thereof, and polyol and oligosaccharide esters thereof.

25. A method in accordance with claim 24 in which said compound is a member selected from the group consisting of dicarboxylic acids having 7 to 13 carbon atoms, mercapto derivatives thereof, salts thereof, and polyol and oligosaccharide esters thereof.

26. A method in accordance with claim 24 in which said compound is a member selected from the group consisting of azelaic acid, the monoglyceride ester and the monosucrose ester thereof.

27. A method for the treatment of skin suffering from hyperhidrosis, ichthyosis vulgaris with or without keratosis pilaris, or wrinkling, said method comprising applying to the affected area a therapeutically effective amount of a dermatological formulation containing from about 5% to about 20% by weight of azelaic acid.

* * * * *